(12) United States Patent
Cuconati et al.

(10) Patent No.: US 9,168,260 B2
(45) Date of Patent: Oct. 27, 2015

(54) BENZODIAZEPINE COMPOUNDS WITH ANTI-FLAVIVIRUS ACTIVITY

(71) Applicants: Baruch S. Blumberg Institute, Doylestown, PA (US); Philadelphia Health & Education Corporation, Philadelphia, PA (US)

(72) Inventors: Andrea Cuconati, Oreland, PA (US); Jinhong Chang, Chalfont, PA (US); Timothy M. Block, Doylestown, PA (US); Ju-Tao Guo, Lansdale, PA (US)

(73) Assignees: Baruch S. Blumberg Institute, Doylestown, PA (US); Drexel University, Philadelphia, PA (US)

( * ) Notice: Subject to any disclaimer, the term of this patent is extended or adjusted under 35 U.S.C. 154(b) by 0 days.

(21) Appl. No.: 14/380,546

(22) PCT Filed: Feb. 22, 2013

(86) PCT No.: PCT/US2013/027241
§ 371 (c)(1),
(2) Date: Aug. 22, 2014

(87) PCT Pub. No.: WO2013/126640
PCT Pub. Date: Aug. 29, 2013

(65) Prior Publication Data
US 2015/0011537 A1    Jan. 8, 2015

Related U.S. Application Data

(60) Provisional application No. 61/603,016, filed on Feb. 24, 2012.

(51) Int. Cl.
*A61K 31/5513* (2006.01)
*C07D 243/24* (2006.01)
*C12Q 1/70* (2006.01)
*C12Q 1/68* (2006.01)

(52) U.S. Cl.
CPC .......... *A61K 31/5513* (2013.01); *C07D 243/24* (2013.01); *C12Q 1/6897* (2013.01); *C12Q 1/70* (2013.01); *G01N 2500/04* (2013.01); *G01N 2500/10* (2013.01)

(58) Field of Classification Search
CPC .................................................. A61K 31/5513
See application file for complete search history.

(56) References Cited

PUBLICATIONS (Lattmann et al. (J. Pharm. Pharmacol. Jun. 2002: 54(6):827-834).*

* cited by examiner

*Primary Examiner* — Valeria Rodriguez-Garcia
(74) *Attorney, Agent, or Firm* — Joseph F. Aceto, Esq.

(57) ABSTRACT

The present invention describes a unique antiviral screen system. The assay is based on quantitatively monitoring viral activation of host cell beta-interferon (IFN-β) gene expression in a HEK293-derived reporter cell line expressing a firefly luciferase gene under the control of a human IFN-β promoter. Unlike the traditional high throughput antiviral assays that measure either the reduction of viral components/yields or cytopathic effect, the readout of the reporter assay in the present invention is the virus-induced host cellular innate immune response. Hence, the assay allows for identification of compounds that inhibit virus infection. In addition, because induction of IFN is one of the most common attributes of viruses, the assay is applicable to all the viruses that are able to infect the reporter cell line and induce IFN-β expression. Compounds that interfere with viral mediated activation of the interferon pathway in a primary screen, can be further screened with virus-specific assay to confirm their antiviral activity.

1 Claim, 7 Drawing Sheets

Control DMSO    USDV-002    USDV-001

BENZODIAZEPINE COMPOUNDS WITH ANTI-FLAVIVIRUS ACTIVITY

CROSS REFERENCE TO RELATED APPLICATIONS

This application claims the benefit of priority of U.S. Provisional Application No. 61/603,016, filed 24 Feb. 2012, and International Application PCT/US2013/027241, filed 22 Feb. 2013 both incorporated herein by reference.

BACKGROUND

Viruses are obligate cellular parasites and rely extensively on hijacking host cellular metabolic machinery for their replication. Meanwhile, virus infection of host cells is recognized by innate pattern recognition receptors that activate cascades of signal transduction pathways leading to production of type I interferons (IFN) and pro-inflammatory cytokines that orchestrate the elimination of the viruses. There is a need to quantitatively monitor viral activation of host cell beta-interferon (IFN-β) gene expression. As shown in FIG. 1, the present invention incorporates, in part, a HEK293-derived reporter cell line expressing a firefly luciferase gene under the control of a human IFN-β promoter (293TLR3/IFNβluc cells). Upon infection, viral genomic RNA and RNA replicative intermediates are recognized by endosomal TLR3 and cytoplasmic RLRs, respectively, and activates signaling cascades resulting in activation of three transcription factors (ATF2/c-Jun, NFκB, IRF3/IRF7), which cooperatively active IFN-β gene (or IFN-β promoter-driven Luc reporter gene) expression.

Unlike the traditional high throughput antiviral assays that measure either the reduction of viral components/yields or cytopathic effect, there is a need to have an assay which provides a direct measure of the virus-induced host cellular innate immune response. Hence, the assay allows for identification of compounds that inhibit virus infection.

SUMMARY

The present invention describes a method for an antiviral screening system. The assay is based on quantitatively monitoring viral activation of host cell beta-interferon (IFN-β) gene expression in a HEK293-derived reporter cell line expressing a firefly luciferase gene under the control of a human IFN-β promoter. Unlike the traditional high throughput antiviral assays that measure either the reduction of viral components/yields or cytopathic effect, the readout of the reporter assay is the virus-induced host cellular innate immune response. Hence, the assay allows for identification of compounds that inhibit virus infection. In addition, because induction of IFN is one of the most common attributes of viruses, the assay is applicable to all the viruses that are able to infect the reporter cell line and induce IFN-β expression. Compounds that interfere with viral mediated activation of the interferon pathway in primary screening can be further screened with a virus-specific assay to confirm their antiviral activity.

Using dengue virus as an example, a "hit" benzodiazepine compound, has been identified from a preliminary screen of 26,900 compounds from a library of more than 86,000 small molecules with anti-flavivirus activity (dengue virus, DENV and yellow fever virus, YFV).

The present method has identified a "hit" benzodiazepine molecule with sub-micromolar antiviral EC50 values and greater than 300 selectivity indexes, against DENV and YFV. Other anti-DENV compounds with different structure have also been identified. The present invention demonstrates that the assay is applicable to effectively identify compounds with antiviral activity. Using the method of the present invention, a family of benzodiazepine compounds is developed into antivirals against one or more of the medically important flaviviruses.

DESCRIPTION OF THE FIGURES

FIG. 7. Structure of a benzodiazepine compound USDV-001.

FIG. 12. Transient DENV replicon transfection assay.

DETAILED DESCRIPTION OF THE INVENTION

Figure 1:
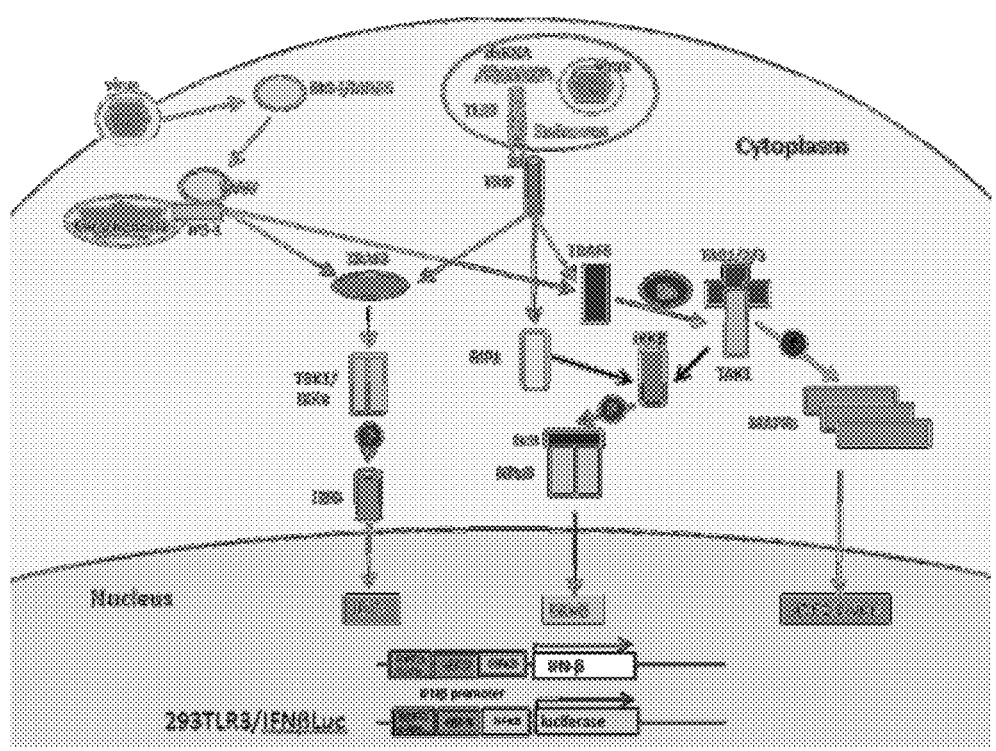
FIG. 1. Model of cellular mechanism showing the activation of the signaling cascade upon infection.
Figure 2:
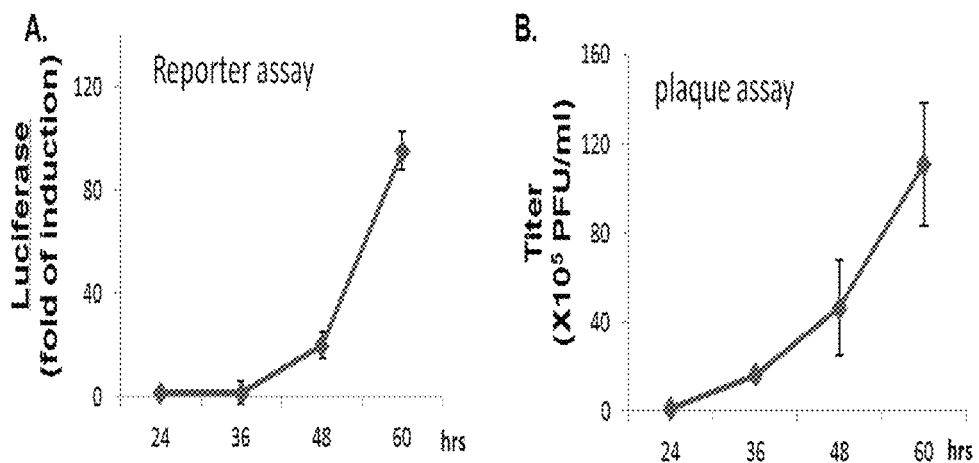
FIG. 2. Graphic representation showing the induction of Luc activity quantitatively correlated with DENV yields.

In one embodiment of the present invention, DENV-induced luciferase expression is quantitatively correlated with the level of DENV replication. To further determine the relationship between viral replication and reporter gene expression, the 293TLR3/IFNβLuc cells were infected with DENV at a MOI of 0.1, the luciferase expression and virus yield were determined at 24, 48 and 60 h post infection. Cells were harvested at the indicated time points post infection to determine luciferase activity and expressed as folds of uninfected controls. Culture media were collected to determine virus yields by plaque assay. As shown in FIG. 2, the levels of luciferase expression (A) are quantitatively correlated with the amount of virus yields (B), demonstrating that the level of virus-induced IFN-β gene expression can quantitatively report the level of viral replication.

Figure 3:
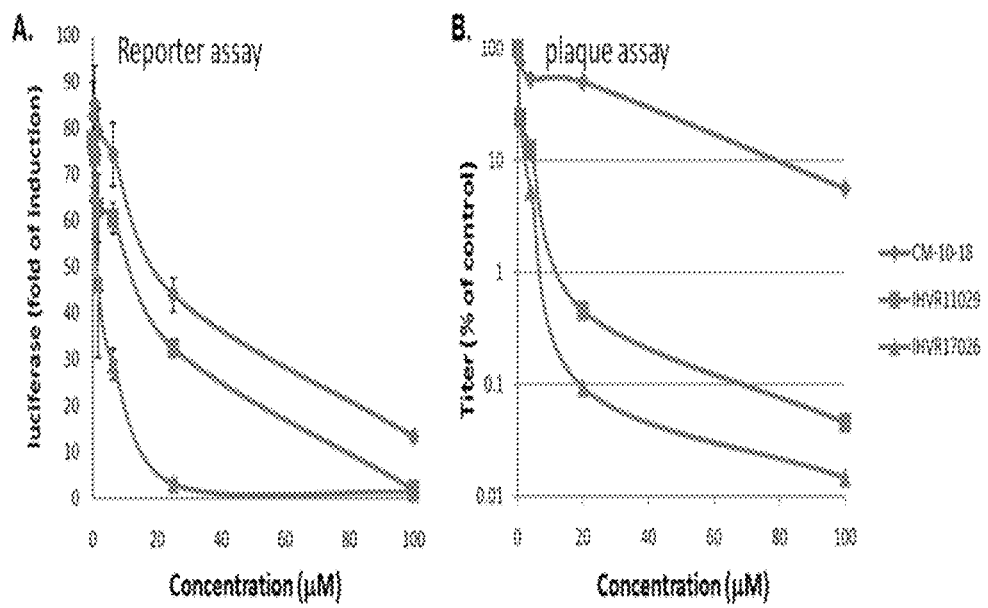
FIG. 3. DENV-induced luciferase expression is dose-dependently inhibited by antiviral compounds. Cells harvested at 60 h post infection and expressed as percentage of untreated controls are shown in A. Virus yields were determined by plaque assay and expressed as percentage of untreated controls shown in B FIG. 4. Flowchart of Library Screening FIG. 5. Plate map for the primary screen FIG. 6. Identification of anti-DENV leads in secondary screening using in-cell western assay.

In another embodiment the method of the present invention is able to identify anti-DENV compounds and show that DENV-induced luciferase expression is dose-dependently inhibited by known antiviral compounds. The observed correlation between the levels of reporter gene expression and innocula size/virus replication shows that the IFN-β promoter driven luciferase reporter assay could be used as a convenient antiviral assay to quantitatively measure antiviral activity of drugs. 293TLR3/IFNβLuc cells were infected with DENV at a MOI of 0.1 and treated with a series dilution of three inmino sugar ER-glucosydase inhibitors that inhibit N-linked glycan processing of virus envelope proteins and thus prevent virion assembly and secretion. Luciferase activity and virus yields were determined at 60 h post infection. As shown in FIG. 3, all three antiviral compounds dose-dependently inhibited both luciferase expression and virus production. More importantly, the potency of the three antiviral compounds was ranked in the same order by the reporter assay and yield reduction assay.

Still in another embodiment of the present invention, a high throughput assay for discovery of antivirals is provided. Using DENV, "hit" molecules with submicromolar or low micromolar EC50s activity have been identified.

EXAMPLE 1

High Throughput Screening

Compound library: 26,900 compounds from a library (Chem-Div Inc.) were tested at a single concentration of 10 micromolar.

Figure 4:
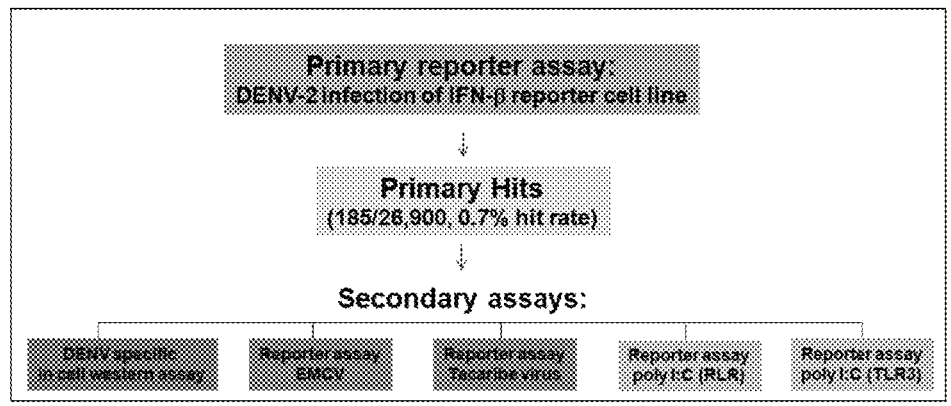
Figure 5:
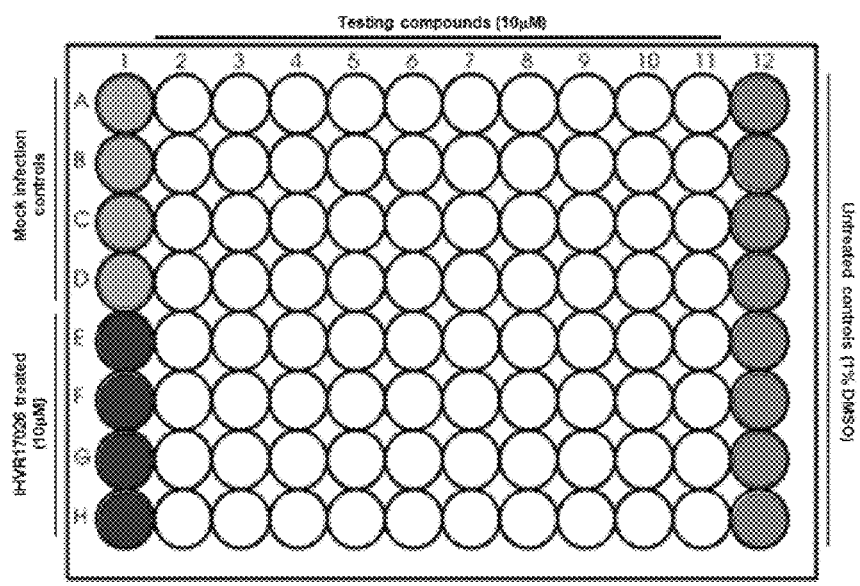

Cell based high throughput screening: A schematic of the screening process is shown in FIG. 4. 293TLR3/IFNβLuc cells were seeded in 96-well black well plates at $2.5 \times 10^4$/ well. A typical plate is shown in FIG. 5. In the primary screening, column 1 of each 96-well plate was mock infected and served as negative controls. Column 12 of each plate was infected with DENV (serotype 2, new Guinea C strain) at a MOI of 0.1 and four wells were treated with 1% DMSO alone (untreated infection controls) and remaining four wells were treated with 10 micromolar IHVR17026 (an imino sugar compound as positive control. See FIG. 3). Each of the remaining 80 wells were infected with DENV and treated with a compound from the compound library at a concentration of 10 micromolar. The cells were harvested at 60 h post infection to measure luciferase activity. The compounds that demonstrated the same or stronger potency, in comparison with the positive control antiviral drug IHVR17026, in reducing luciferase expression were considered as primary "hits".

To validate the primary screening results, each of the primary "hits" was re-tested in a 96-well plate format at a serial dilution ranging from 10 to 0.3 micromolar in triplicates. Each testing plate also contains eight wells treated with 1% DMSO (untreated infection controls) and 8 wells treated with positive control compound (IHVR17026) at a serial dilution ranging from 10 to 0.3 micromolar. DENV infection and luciferase assay were performed as described for the primary screening assay. An additional set of drug treated plates, without DENV infection, were incubated for 60 h and cell viability were determined with a MTT assay (Sigma).

185 compounds that had $EC_{50}$ values of less than 10 micromolar, but reduced cell viability less than 25% at 10 micromolar, and dose-dependently reduced DENV-induced luciferase expression, were considered as confirmed "hits".

Principle of this reporter assay predicts that the "hits" from the reporter assay can be potential inhibitor of DENV. To validate the antiviral activity and spectrum of activity, we at first tested the antiviral activity of all the confirmed "hits" with an In-cell western assay that detects viral envelope (E) protein accumulation in virally infected human hepatoma cells (Huh7.5). FIG. 6 shows the identification of two lead anti-DENV compounds in such secondary anti-viral screening. Huh7.5 cells were seeded into 96-well plates and infected with DENV-2 at an MOI of 0.1. The infected cells were left untreated or treated with the indicated concentrations of selected compounds for 48 h. Cells were then fixed and DENV envelope protein expression was revealed by immunostaining (left column) and cell viability was determined by Sapphire 700 staining (right column).

Additional reporter assays using 293TLR3/IFNβLuc cells infected with two viruses from virus families that are distinct from DENV, the encephalomyocarditis virus (EMCV) and tacaribe virus (TARV) were performed. This is aimed to identify compounds with broad-spectrum antiviral activity. Moreover, two reporter assays using 293TLR3/IFNβLuc cells treated with RIG-I and TLR3 signaling ligands were performed, to rule out those compounds that reduced IFN-β reporter through non-antiviral innate immune regulation. From these complex secondary screenings, 3 "hits" with specific anti-dengue virus activities were identified.

EXAMPLE 2

Identification and Characterization of Hits with Specific Anti-Dengue Virus Activity 26,900 unique compounds were screened. After the secondary screening, three compounds were identified with specific anti-dengue virus activity, but not active against EMCV or TARV. The structure of a benzodiazepine compound, USDV-001, is shown in FIG. 7.

Figure 8:
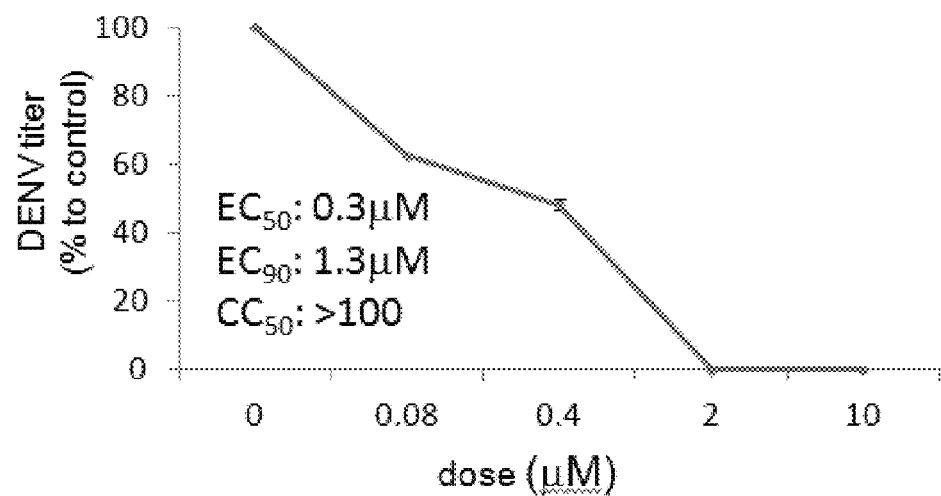
FIG. 8. Anti-DENV activity of USDV-001 in yield reduction assay.

The antiviral activity of USDV-001 against DENV was further confirmed with a more specific virus yield reduction assay in a human hepatoma cell line Huh7.5. As shown in FIG. 8, USDV-001 has an EC50 of 0.3 micromolar, EC90 of 1.3 micromolar and CC50 of greater than 100 micromolar, resulting an selectivity index of greater than 300, against DENY. Huh7.5 cells were infected with DENV-2 at an MOI of 0.01. The infected cells were left untreated or treated with USDV-001 at indicated concentrations for 48 h. Tissue culture media were harvested and standard plaque assays were performed in Vero cells to determine the DENV titers.

EXAMPLE 3

Antiviral Spectrum Against Other Viruses from Flaviviridae Family

Figure 9:
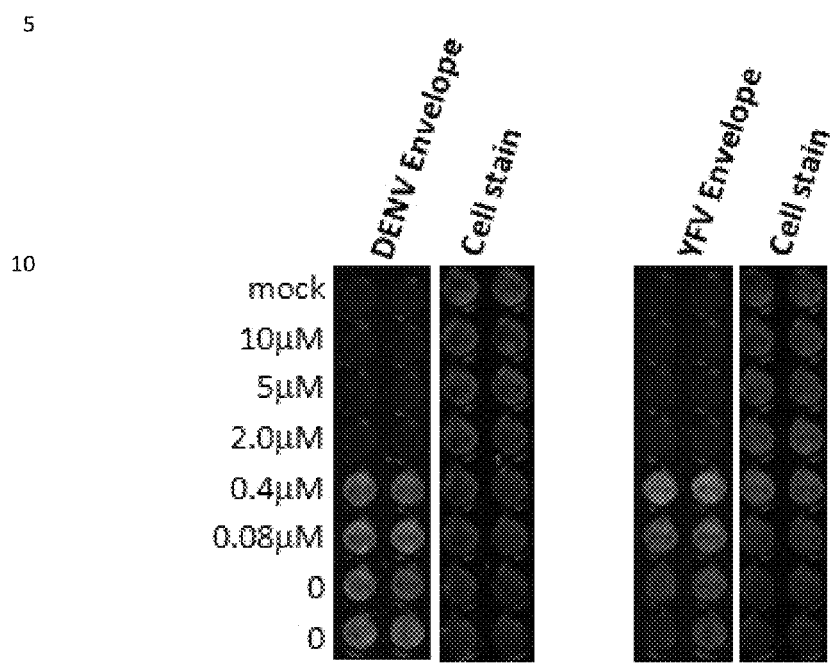
FIG. 9. Anti-DENV and anti-YFV activity of USDV-001 in in-cell western assay.

Another embodiment shows that USDV-001 is also active against YFV (17D vaccine strain), which belongs to the same genus with DENV (flavivirus genus). The antiviral potency against DENV and YFV is very similar in an in-cell western assay (FIG. 9). Huh7.5 cells were seeded into 96-well plates and infected with DENV-2 or YFV (17D), each at an MOI of 0.1. The infected cells were left untreated or treated with the indicated concentrations of USDV-001 for 48 h. Cells were then fixed and DENV or YFV envelope protein expression was revealed by immunostaining (green) and cell viability was determined by Sapphire 700 staining (red). Experiment was performed in duplex.

Figure 10:
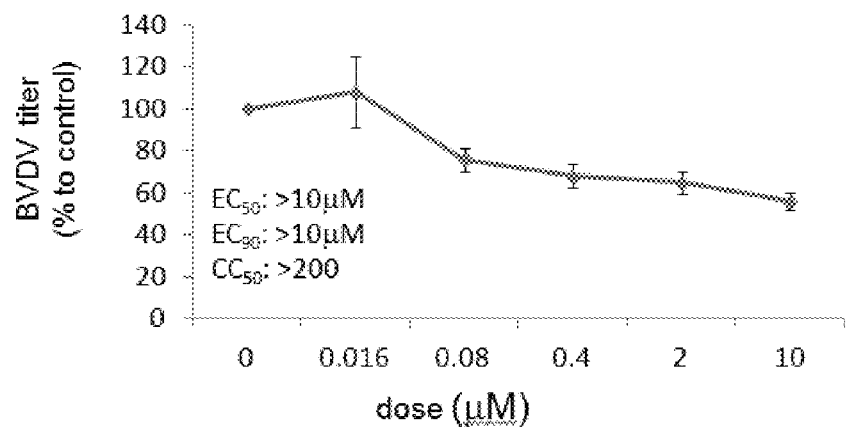
FIG. 10. Anti-BVDV activity of USDV-001 in yield reduction assay.

USDV-001's antiviral activity against another member of flaviviridae was also tested such as Bovine viral diarrhea virus (BVDV, NADL strain), which belongs to pestivirus genus. As shown in FIG. 10, USDV-001 does not have significant anti-BVDV activity. MDBK cells were infected with BVDV at an MOI of. The infected cells were left untreated or treated with USDV-001 at indicated concentrations for 24 h. Tissue culture media were harvested and standard plaque assay were performed in MDBK cells to determine the virus titers.

These results indicated that USDV-001 is likely to be specific against flaviviruses (DENV and YFV).

Mechanism-of-Action of Hit Compounds

Figure 11:
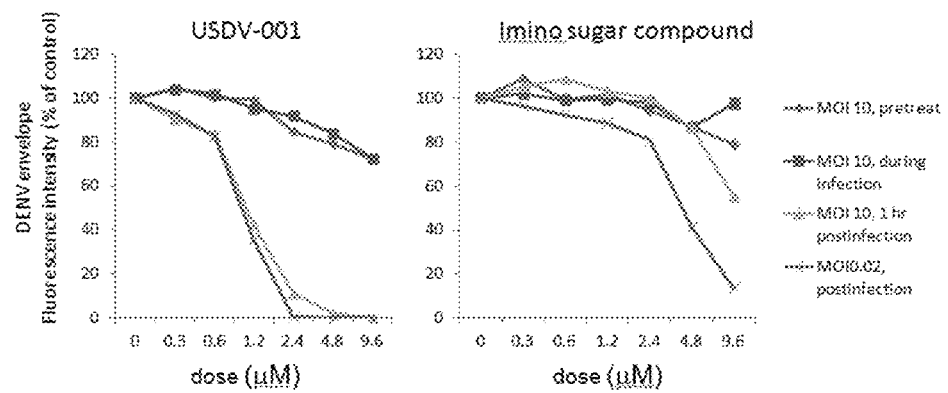
FIG. 11. Time-of-addition experiment using in-cell western assay.

Time-of-addition experiment was performed using in-cell western assay (FIG. 11). Huh7.5 cells were seeded into 96-well plates and infected with DENV-2 at either high (10) or low (0.02) MOI. The infected cells were left untreated or treated with the indicated concentrations of either USDV-001 or control imino sugar compound, at indicated time period. Cells were then fixed and DENV envelope protein expression was revealed by immunostaining, 48 h postinfection. The fluorescence intensities corresponding to DENV envelope expression were quantified using LI-COR software, and expressed as percentage relative to no treatment control.

Some cells were infected with high MOI of DENV. Pre-treatment of the cells for 2 hr prior to infection, or treatment of the cells for 1 hr during the infection did not have an antiviral effect, indicating USDV-001 does not inhibit dengue virus through blocking of early life cycle of virus replication, e.g. attachment and entry steps. Treatment immediately after infection showed significant inhibition of DENV replication, as judged by significant decrease of DENV envelope. A control experiment using low MOI of DENV infection and an imino sugar compound, which is known to inhibit the virion secretion step, were included as control. Overall, these results indicate that USDV-001 interferes with DENV replication at intracellular step(s), e.g. uncoating, translation, or genome RNA replication, other than entry or virion secretion.

Figure 12:
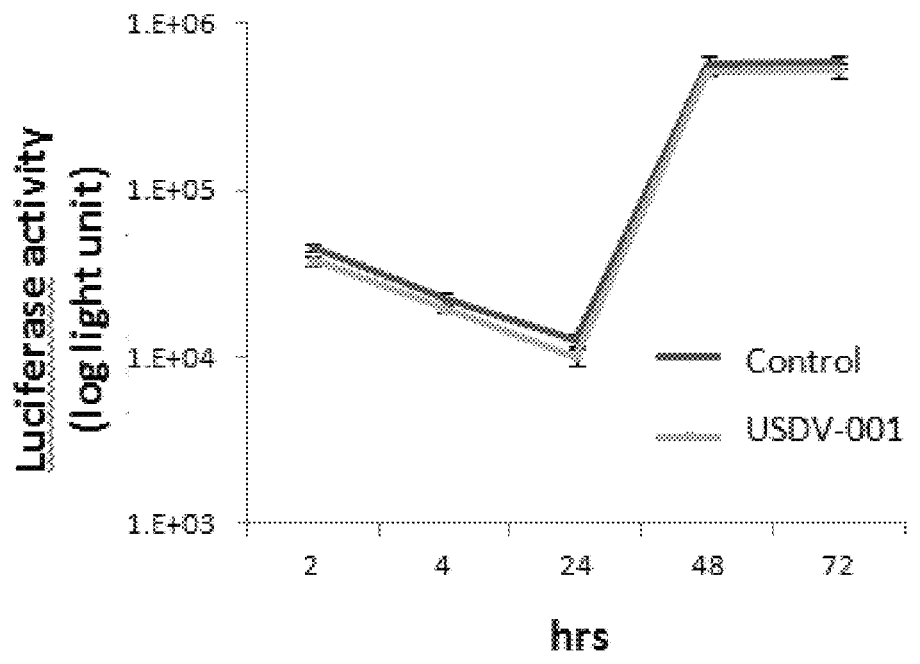

To further map the step(s) affected by USDV-001, a transient DENV replicon assay was performed (FIG. 12). DENV serotype 2 replicon RNA containing a *Renilla* luciferase reporter was electroporated into Huh7.5 cells and seeded into 24-well plates. Cells were left untreated or treated with 10 mM of USDV-001. Luciferase activities were assayed at indicated time post transfection. The $\text{Log}_{10}$ values of average luciferase activities and standard deviations are plotted. In this experiment, the first luciferase peak (~2 h post electroporation) indicates the protein translation from the input DENV replicon genome, and the second luciferase peak (~48 h post electroporation) indicates the protein synthesis as a result of genome replication. This experiment clearly shows that USDV-001 affects neither translation nor genome replication.

Based on these mechanism-of-action studies, USDV-001 affects either a step after entry and before translation, for example, uncoating, or the stability of DENV envelope protein stability (which component is missing from replicon). Successful selection of resistant mutants might lead to the identification of viral target for USDV-001.

The present invention, in part, provides a method to identify a benzodiazepine compound, USDV-001 with potent anti-DENV and YFV activity. This compound serves as lead for the development of benzodiazepine family compounds for flavivirus therapeutics.

Although the present invention has been described with reference to specific embodiments, workers skilled in the art will recognize that many variations may be made therefrom, for example in the particular selection of a detection molecule linked to AAL herein described, and it is to be understood and appreciated that the disclosures in accordance with the invention show only some preferred embodiments and advantages of the invention without departing from the broader scope and spirit of the invention. It is to be understood and appreciated that these discoveries in accordance with this invention are only those which are illustrated of the many additional potential applications that may be envisioned by one of ordinary skill in the art, and thus are not in any way intended to be limiting of the invention. Accordingly, other objects and advantages of the invention will be apparent to those skilled in the art from the detailed description together with the claims.

We claim:

1. A method for treating a flavivirus infection, said method comprising administering to an infected subject an effective amount of at least one compound of the formula (I) or a pharmaceutically acceptable salt;

(I)

wherein the flavivirus infection is dengue virus or yellow fever virus.

* * * * *